(12) United States Patent
Peters et al.

(10) Patent No.: US 11,402,349 B2
(45) Date of Patent: Aug. 2, 2022

(54) HIGH CAPACITY REDOX ELECTRODES AND THEIR USE IN CELL LYSIS

(71) Applicant: Global Life Sciences Solutions Operations UK Ltd, Sheffield (GB)

(72) Inventors: Andrea Jeannine Peters, Niskayuna, NY (US); Thomas Elliot Stecher, Niskayuna, NY (US); Craig Patrick Galligan, Niskayuna, NY (US); Christopher Michael Puleo, Niskayuna, NY (US); Ralf Lenigk, Niskayuna, NY (US)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 518 days.

(21) Appl. No.: 15/532,233

(22) PCT Filed: Dec. 3, 2015

(86) PCT No.: PCT/EP2015/078496
§ 371 (c)(1),
(2) Date: Jun. 1, 2017

(87) PCT Pub. No.: WO2016/087575
PCT Pub. Date: Jun. 9, 2016

(65) Prior Publication Data
US 2017/0363561 A1    Dec. 21, 2017

Related U.S. Application Data

(63) Continuation of application No. 14/559,673, filed on Dec. 3, 2014, now abandoned.

(51) Int. Cl.
*G01N 27/30* (2006.01)
*C12M 1/00* (2006.01)
(Continued)

(52) U.S. Cl.
CPC ............ *G01N 27/30* (2013.01); *C12M 47/06* (2013.01); *G01N 27/453* (2013.01);
(Continued)

(58) Field of Classification Search
CPC ...... G01N 27/30; G01N 27/453; H01G 9/042; H01G 9/22; H01G 11/02; H01G 11/28; H01G 11/48; H01G 11/86
(Continued)

(56) References Cited

U.S. PATENT DOCUMENTS 5,399,245 A * 3/1995 Fedkiw, Jr. ............... C25B 1/00
                                                            205/334
2002/0142202 A1* 10/2002 Li ........................ H01M 4/624
                                                            429/406
(Continued)

FOREIGN PATENT DOCUMENTS

EP         1484809 A1   12/2004
WO   2004/032162 A1    4/2004
(Continued)

OTHER PUBLICATIONS

Wistrand et al., "Preparation of electrically conducting cellulosefibres utilizing polyelectrolyte multilayers ofpoly(3,4-ethylenedioxythiophene):poly(styrene sulphonate)and poly(allyl amine)", 2007, European Polymer Journal, 43, 4075-4091 (Year: 2007).*

(Continued)

*Primary Examiner* — Vincent Tatesure
(74) *Attorney, Agent, or Firm* — Eversheds Sutherland (US) LLP

(57) ABSTRACT

The present disclosure relates to the manufacture and use of redox electrodes and their use in cell lysis. In certain embodiments, the redox electrodes are manufactured using a hybrid material approach, such as using a redox polymer (Continued)

in combination with a support substrate, such as cellulose fibers or paper. In certain implementations, the redox electrodes are suitable for use at voltages greater than 25 Volts.

7 Claims, 5 Drawing Sheets

(51) Int. Cl.
  *H01G 9/042* (2006.01)
  *H01G 9/22* (2013.01)
  *H01G 11/02* (2013.01)
  *H01G 11/28* (2013.01)
  *H01G 11/48* (2013.01)
  *H01G 11/86* (2013.01)
  *G01N 27/453* (2006.01)
  *H01M 4/60* (2006.01)

(52) U.S. Cl.
  CPC ............... *H01G 9/042* (2013.01); *H01G 9/22* (2013.01); *H01G 11/02* (2013.01); *H01G 11/28* (2013.01); *H01G 11/48* (2013.01); *H01G 11/86* (2013.01); *H01M 4/602* (2013.01); *Y02E 60/13* (2013.01)

(58) Field of Classification Search
  USPC .......................................................... 442/59
  See application file for complete search history.

(56) References Cited

U.S. PATENT DOCUMENTS

| 2007/0109722 A1 | 5/2007 | Ohmori |
| 2007/0131910 A1* | 6/2007 | Daniel .................. C08L 31/04 |
| | | 252/500 |
| 2012/0219987 A1 | 8/2012 | Mussivand et al. |
| 2013/0102706 A1 | 4/2013 | Alsewailem |

FOREIGN PATENT DOCUMENTS

| WO | 2011/081944 A2 | 7/2011 |
| WO | 2014/135877 A1 | 9/2014 |

OTHER PUBLICATIONS

PCT International Search Report and Written Opinion for PCT Application No. PCT/EP2015/078496 dated May 18, 2016 (14 pages).

Shigehara et al., "Electrochemical Responses of Electrodes Coated with Redox Polymers. Evidence for Control of Charge-Transfer Rates Across Polymeric Layers by Electron Exchange between Incorporated Redox Sites," J. Am. Chem. Soc., 1981, 103:2552-2558.

Vazquez et al., "Solution-Cast Films of Poly(3,4-Ethylenedioxythiophene) as Ion-to-Electron Transducers in All-Solid-State Ion-Selective Electrodes," Sensors and Actuators B, 2004, 97:182-189.

* cited by examiner

US 11,402,349 B2

HIGH CAPACITY REDOX ELECTRODES AND THEIR USE IN CELL LYSIS

CROSS REFERENCE TO RELATED APPLICATIONS

This application claims the priority benefit of PCT/EP2015/078496 filed on Dec. 3, 2015 which claims priority benefit of U.S. application Ser. No. 14/559,673 filed Dec. 3, 2014. The entire contents of which are hereby incorporated by reference herein.

BACKGROUND

The subject matter disclosed herein relates to oxidation-reduction (redox) polymers, their manufacture, and use, for example in cell lysis.

Redox polymers are highly regarded electrode materials for many research fields, including basic polymer science, electronics and optoelectronics, photovoltaics, capacitors, rechargeable batteries, biosensors, and novel cell systems. In particular, redox polymers may have properties that include high conductivity, high stability, and/or good optical transparency, which may be useful in these fields.

The redox polymers can exist in a conducting state, where the polymer is doped to allow formation of positive charges along the conjugated backbone. Anions from a supporting electrolyte or anionic copolymer allow the redox polymer to function as an electrode material. In the majority of applications these materials are currently used in, only low voltages (e.g., less than 5 V) are required and applied to the films. Applying potentials much greater than the oxidation potential of the redox polymer (i.e., over-oxidation) results in the degradation of the conducting films. Therefore, typically in thin films of redox polymers, only low voltages can be applied to the film to prevent decomposition of the film, which would render the film electrochemically inactive, destroying the electrode.

Further, with respect to the manufacture of such electrodes, industrial application of common conductive polymers, such as polythiophenes, polypyrroles and polyanilines, has been limited due to the poor mechanical properties and processability of the polymeric material. In general these polymers are only slightly soluble in aqueous and most common organic solvents, making solution processing techniques for film formation difficult. Additionally, thick films formed from the conducting polymers are generally brittle and therefore do not have good mechanical properties.

BRIEF DESCRIPTION

In one embodiment, an oxidation-reduction (redox) electrode is provided. In accordance with this embodiment, a support substrate is provided. A redox polymer is coated on or combined with the support substrate.

In a further embodiment, a method for manufacturing a redox electrode is provided. In accordance with this embodiment, an aqueous dispersion of a redox polymer is blended with cellulose fibers to form a slurry. The slurry is solution cast into one or more molds each having a form factor corresponding to the redox electrode to form a respective redox electrode in each mold. The respective redox electrode is recovered from each mold.

In an additional embodiment, a method for manufacturing a redox electrode is provided. In accordance with this embodiment, a cellulose paper substrate is dip coated in an aqueous dispersion of a redox polymer one or more times. The redox electrode is formed using the dip coated cellulose paper.

In another embodiment, a method for manufacturing a redox electrode is provided. In accordance with this embodiment, an aqueous dispersion of a redox polymer is solution cast onto a cellulose paper substrate. The redox electrode is formed using the solution cast onto the cellulose paper. Additional embodiments are concerned with the use redox electrodes for cell lysis.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
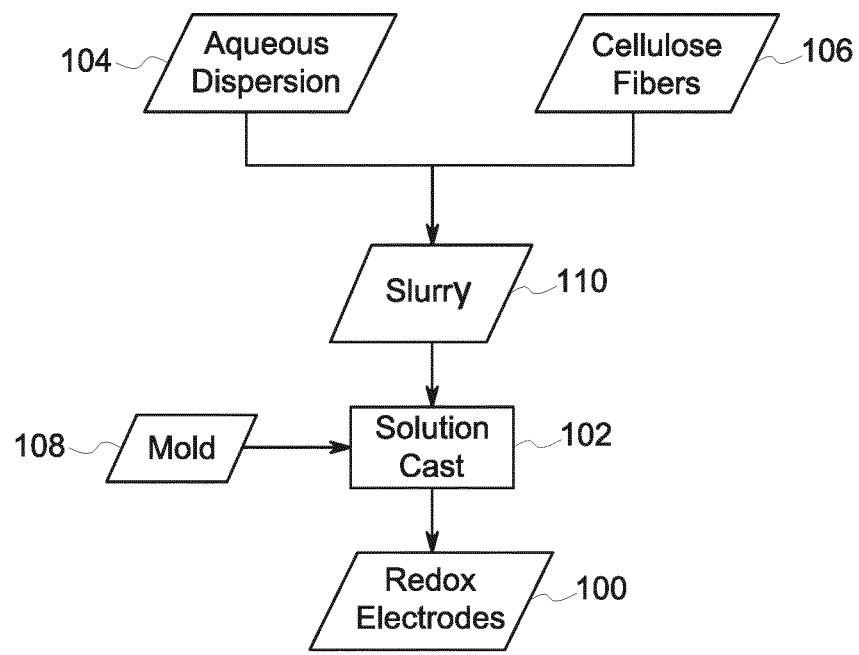
FIG. 1 depicts a process flow diagram describing one embodiment of a redox electrode manufacturing process, in accordance with aspects of the present disclosure.
Figure 2:
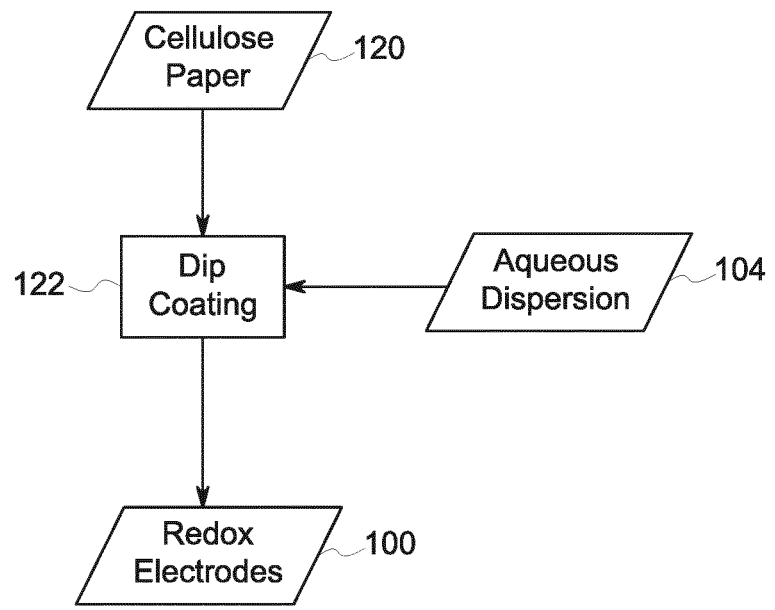
FIG. 2 depicts a process flow diagram describing a further embodiment of a redox electrode manufacturing process, in accordance with aspects of the present disclosure.
Figure 3:
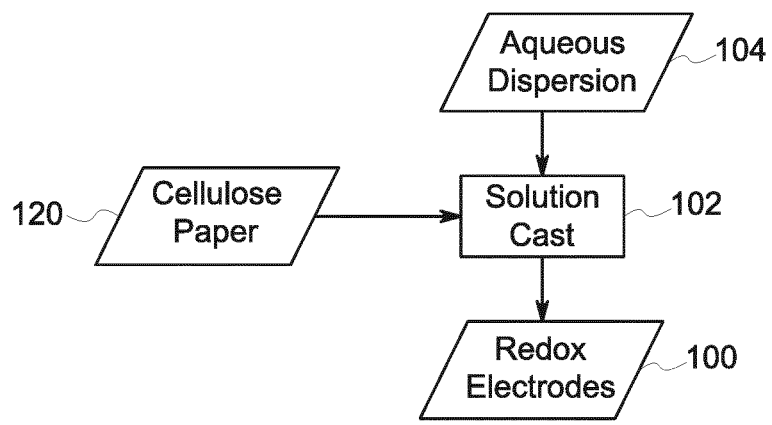
FIG. 3 depicts a process flow diagram describing an additional embodiment of a redox electrode manufacturing process, in accordance with aspects of the present disclosure.

Oxidation-reduction (redox) polymers, such as the conjugated polythiophene polymer poly(3,4-ethylenedioxythiophene) (PEDOT), are useful as electrode materials for a variety of purposes, including basic polymer science, electronics and optoelectronics, photovoltaics, capacitors, rechargeable batteries, biosensors, and novel cell systems. Electrodes formed using these polymer materials provide high conductivity, high stability, and/or good optical transparency. In most of the applications these materials are currently used in, only low voltages (e.g., less than 5 V) are applied to the films due to higher potentials potentially causing over-oxidation and corresponding degradation of the conducting film. Therefore, only low voltages can be applied to the thin-film redox polymers in order for prevent decomposition of the film that would render the film electrochemically inactive.

In addition, industrial processing of common conductive polymers, such as polythiophenes, polypyrroles and polyanilines, is typically limited due to poor mechanical properties and processability of the polymeric material. For example, the polymers may be only slightly soluble in aqueous and most common organic solvents, making solution processing techniques for film formation difficult. Additionally, thick films formed from the conducting polymers are generally brittle and therefore do not have good mechanical properties. For example, a redox polymer applied in a thickness greater than 1 micron may lose mechanical integrity, and may therefore be subject to mechanical breakdown or degradation. Additionally, thin film electrodes comprised of these redox polymer materials, have limitations to the amount of charge that the electrode can pass. The number of available redox polymer molecules in an electrode limits the charge that an electrode can transfer. For certain applications, it is important that a large charge can be transferred at a high voltage. This task cannot be achieved by current industrial electrode fabrication methods, such as the casting of thin films onto flexible plastic supports.

As discussed herein, improvements to mechanical properties of the redox polymers can be accomplished by creating hybrid materials, in which the conducting polymer can be coated onto or otherwise combined with other textile fibers (e.g., paper), plastics, or polymers. In particular, as discussed herein, a variety of solution casting and dip coating approaches are discussed that are suitable for creating redox electrodes having thickness greater than 1 micron with respect to the surface of an underlying substrate composed of respective substrate particles or fibers. Such redox electrodes may be suitable for use in high capacity applications.

In particular, the present disclosure relates: A) the composition and manufacture of electrodes that include redox polymers on a cellulose support; and B) the use of redox electrodes as discussed herein, as high capacity electrodes for applications employing high voltages (e.g., 25 V to 1,000 V).

For example, in an application involving the lysis of cells from biological samples (e.g., red or white blood cells), the presently disclosed redox polymer electrodes can be used in a device to establish a high electric field strength, generated using high voltages (up to 1,000 V), across a fluid channel resulting in cell lysis. One advantage of using high capacity redox electrodes over standard metal electrodes (Pt, Cu, Au, and so forth) is the ability to maintain these high voltages over long periods of time (e.g. minutes or tens of minutes) without forming undesirable gases from water electrolysis that would occur between a standard metal electrodes and the aqueous electrolyte, which would ultimately affect the device performance. An additional advantage is that the present redox polymer electrodes may be fabricated so as to be biocompatible with tissues and systems of interest as a consequence of the cross-linking procedure, discussed in greater detail below.

With the preceding in mind, the composition and manufacturing process for a redox electrode in the form of a paper electrode is disclosed. Paper redox electrodes as discussed herein generally include a conjugated polymer and a solid support. As discussed herein, the redox polymers can exist in a conducting state, where the polymer is doped to allow formation of positive charges along the conjugated backbone. Anions from a supporting electrolyte or anionic copolymer (such as polystyrene sulfonate (PSS)) allow the redox polymer to function as an electrode material. In certain implementations, the presently disclosed redox electrodes are formed from a redox polymer (e.g., PEDOT:PSS, conjugated polyaniline polymer and/or the conjugated polypyrrole polymer), a solid support (e.g., cellulose fibers), an ionic cross-linking agent (e.g., MgSO4), and may include an optional coating, such as an ionomer coating (e.g., Nafion™).

Turning to FIG. 1, in a first embodiment, redox electrodes 100 may be manufactured by solution casting (block 102) films of a PEDOT:PSS aqueous dispersion 104 blended with cellulose fibers 106. Various form factors of the electrodes 100 can be manufactured using this method (e.g., rods) by casting the solution into molds 108 of desired shape. As noted above, redox electrodes 100 formed in this manner may have a thickness greater than 1 micron relative to the underlying substrate surface.

By way of example, in this embodiment, an aqueous dispersion 104 of PEDOT:PSS (e.g., 1.0 wt %-1.3 wt %) blended with raw cellulose fibers 106 (10 μm to 5000 μm in length, which may be purchased in fiber form or generated through a ball milling process of cellulose paper). The PEDOT:PSS aqueous dispersion 104 is blended with the cellulose fibers to produce a slurry 110 that can be solution cast (block 102) into molds 108 to produce the electrodes 100 of different dimensions and form factors, as determined by the dimensions of the molds 108. The proportion of PEDOT:PSS to cellulose fibers 106 can be varied in the slurry 110 to customize the composition of the redox electrodes 100. In one example, a slurry 110 containing 5%-25% (by weight) PEDOT:PSS (e.g., 14%-18% by weight PEDOT:PSS) relative to cellulose 106 is cast into ring molds onto glass plates to form films of thicknesses that vary between 250 nm-500 nm thick. Overall surface resistance values obtained for the film in such an implementation range from 900Ω-2000Ω (at 4 mm probe distance).

The thicknesses (i.e., three-dimensionality) of the redox electrodes 100 can be controlled by varying the composition and amount of slurry 110 that is cast into the molds 108. Control of these factors (e.g., thickness and other dimensions of the electrodes 100 as well as the percentage of PEDOT:PSS relative to cellulose) allows for tailoring of the composition and dimensions of the redox electrode 100 to obtain optimal performance for various applications or devices. For example, increasing the proportion of PEDOT:PSS will increase charge capacity of electrodes 100, with the charge capacity being selected based on the application for which the electrodes will be used.

As noted above, alternative form factors for the electrode 100 can be obtained using the PEDOT:PSS/cellulose fiber slurry 110 by casting (block 102) the solution into molds 108 of specific dimensions. In one example the PEDOT:PSS slurry 110 is cast into a coupon with defined well dimensions (e.g., 1 mm deep) to produce PEDOT:PSS paper electrodes 100 of specific height/width/depth dimensions. Additionally, cylindrical PEDOT:PSS/cellulose electrodes can be prepared. For example, in one implementation, heat shrink wrap is filled with premade PEDOT:PSS/cellulose electrodes 100 that had been moistened with distilled water and heated at 100° C.

As discussed in greater detail below, in addition to forming electrodes 100 of different form factors and having a substantive thickness or three-dimensional character (in contrast to conventional surface coating techniques), the redox electrodes 100 may also be formed around metal (e.g., copper or gold) wires and mesh. Such implementations allow for a variation in the surface area contact between PEDOT:PSS/cellulose material and the wire that carries the potential being delivered from a power source. In particular, increasing the contact area between wire and the redox electrode 100 allows for greater access to the redox sites in the porous PEDOT:PSS paper electrode and allows for an increase in current capacity.

In a second embodiment, instead of solution casting, a dip coating approach may be employed. In one such embodiment, cellulose paper 120 cut to a desired dimension (e.g., Whatman 31 ETF paper) may be dip coated (block 122) into a PEDOT:PSS aqueous dispersion 104. In one such implementation, the cellulose paper may be dipped into the aqueous dispersion 104 for a length of time that yields the desired thickness of film forming the electrode 100 and yields the desired resistance values of the film. In other implementations, the cellulose paper 120 may be repeatedly dipped in the aqueous dispersion 104 to obtain the desired thickness and resistance values of the film that will form the redox electrode 100. By way of example, in one test, after four dip coat applications and drying processes, a uniform PEDOT:PSS coated cellulose paper was obtained suitable for use as an electrode 100 and having a resistance of less than 1 k$\Omega$ (at 4 mm probe distance).

In a third embodiment, another solution casting approach may be employed. In this embodiment, a PEDOT:PSS aqueous dispersion 104 is solution cast (block 102) onto cellulose paper 120 (e.g., Whatman 31 ETF paper) until desired thickness of film and resistance values of film are obtained to form redox electrodes 100. In one implementation, the cellulose paper 120 is housed in an aluminum frame and heated at high temperature (e.g., 100° C.-150° C.). In this example, after six coats (e.g., three on each side), followed by drying and cross-linking, a uniform PEDOT:PSS coated cellulose paper was obtained suitable for use as a redox electrode 100 and having a resistance of less than 1 k$\Omega$ (at 4 mm probe distance).

Figure 4:
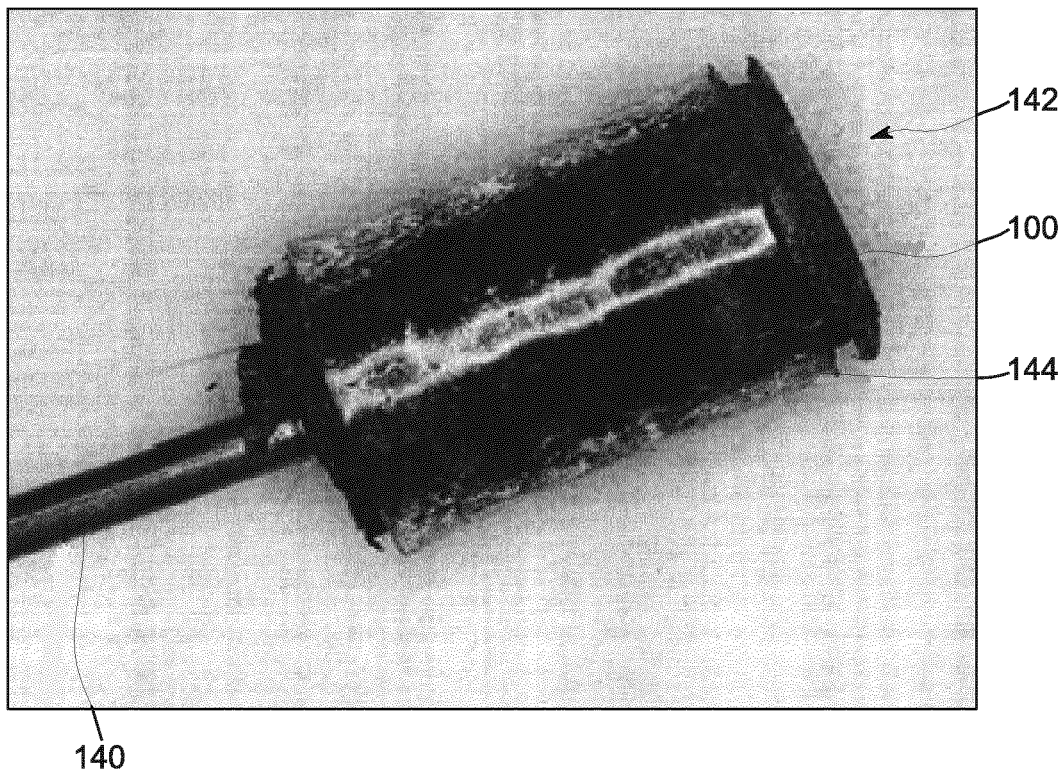
FIG. 4 depicts a cylindrical electrode disposed about a wire, in accordance with aspects of the present disclosure.

With the preceding discussion of manufacturing approaches in mind, and turning to FIG. 4, in certain embodiments the surface area of the lead or wire 140 (e.g., copper wire) that is in contact with the PEDOT:PSS electrode may be increased. By way of example, a copper wire 140 was inserted approximately ¾ of the way into a cylindrical PEDOT:PSS/cellulose electrode 142, such as an electrode prepared by packing heat shrink wrap 144 with moistened PEDOT:PSS cellulose electrodes 100 and heating. In such an approach, the wire 140 is in contact with the PEDOT:PSS material through the center of the electrode 142 as opposed to just having surface contact with the tip of one end.

Figure 5:
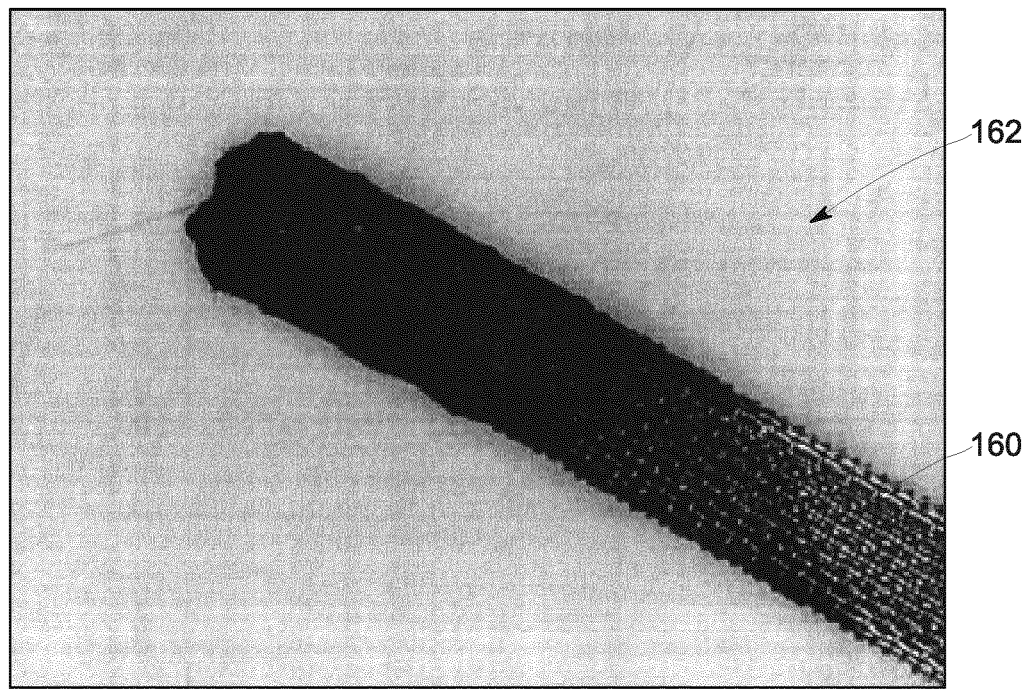
FIG. 5 depicts a dip coated mesh or foil, in accordance with aspects of the present disclosure.

In another example, and turning to FIG. 5, a foil or mesh substrate 160 (e.g., a copper foil or mesh) may be dip coated using a PEDOT:PSS/cellulose fiber slurry 110 to obtain a PEDOT:PSS paper electrode coated foil 162. Such a coated foil or mesh substrate provides a high surface area of contact between the substrate (e.g., copper) and PEDOT material.

While the preceding relates to various manufacturing approaches, certain example and experimental results are now set forth demonstrating the use of redox electrodes manufactured using the approaches discussed herein.

First Experiment:

Materials: Clevios PH 1000 (purchased from Hereaus and used without further purification) was used as the source of PEDOT:PSS (aq). Whatman 31 ETF cellulose paper was used (obtained from Whatman).

General Preparation of PEDOT:PSS/Cellulose Electrodes:

(1) Solution casting films from PEDOT:PSS aqueous dispersion blended with cellulose fibers (e.g., 5-25 wt % (such as 14-18 wt %) PEDOT:PSS): Cellulose fibers were obtained through a ball milling process of Whatman 31 ETF cellulose paper. 1"×1" pieces of cellulose paper were added to a 4 L glass jar and filled with 2 L of distilled water. Small glass beads (0.5 mm diameter) were added and the jar was sealed. The contents of the jar were put on a lab roller and mixed for 24-48 hours, or until the cellulose paper had broken down into its component fibers. The fibers were isolated by vacuum filtration through a fritted glass filter, washed with distilled water (2×250 mL) and allowed to air dry. To a 2 dram vial was added 1.5 g of dry cellulose fibers and 15 g of Clevios PH 1000. The vial was sealed and placed on the lab roller for 15 minutes to ensure complete mixing of the PEDOT:PSS with the cellulose fibers. 11.1 g of the mixture was cast into a glass ring (diameter=6.4 cm) on a glass plate and the water was allowed to evaporate at room temperature for 3 days. The films were removed from the glass ring and plate and had an average thickness of 265 nm and demonstrated a resistance of 1,850$\Omega$.

Cross-linking of the film was done by punching out 4 mm disks of the film and soaking them in a 0.25 M MgSO4 (aq) solution for 1 hour. The disks were removed from solution, placed on Teflon coated aluminum foil and dried in an oven for 1 hour at 60° C. A second cross-linking step was performed by soaking the disks in a fresh solution of 0.25 M MgSO4 (aq) for 1 hour. The disks were removed, placed on Teflon coated aluminum foil and dried in an oven for 1 hour at 60° C.

(2) Dip coating cellulose paper into PEDOT:PSS dispersion (aq): Whatman 31 ETF cellulose paper was cut into 3.5"×1" strips and tapered to fit into the bottom of a 50 mL centrifuge tube. A 50 mL centrifuge tube was filled with PEDOT:PSS (aq) solution (Clevios PH 1000) and the cellulose paper, equipped with a hanger clip, was dipped into the solution and allowed to soak for 1 minute. The paper was removed from solution and hung in a convection oven at 80° C. for 20 minutes to dry. The paper was dipped in the solution and dried three more times for a total of 4 coats. The PEDOT:PSS coated cellulose paper was cross-linked by soaking in a 0.25 M MgSO4 (aq) solution for 1 hour. It was then removed from solution and dried in a convection oven at 80° C. for 20 minutes. 4 mm disks were punched out and the disks were further cross-linked by soaking in a 0.25 M MgSO4 (aq) solution for 1 hour. The disks were removed from solution and dried in a convection oven at 80° C. for 20 minutes.

(3) Solution casting a PEDOT:PSS (aq) dispersion onto cellulose paper: A 2.5"×2.5" piece of Whatman 31 ETF cellulose paper was cut and mounted to an aluminum frame. The frame was positioned on a hotplate set at 130° C. (~1" gap between hotplate and cellulose paper). 2 mL of Clevios PH 1000 was evenly applied to the paper and allowed to dry for 15 minutes. The frame was turned over and another 2 mL of Clevios PH 1000 was evenly applied to the paper. A paintbrush was used to spread out any solution that pooled on the surface. This was allowed to dry for 15 minutes. This process was repeated until each side has been coated 3 times with the PEDOT:PSS solution. 80% EtOH solution was applied to the dry film on the hotplate to soak (~2 mL) and heat until dry (~20-30 minutes). The dry film was removed from the frame and placed in a 0.25 M $MgSO_4$ (aq) solution and allow to soak for 1 hour. This was removed from solution and placed in an oven at 60° C. for 1 hour. 4 mm disks were punched out and placed in a 0.25 M $MgSO_4$ (aq) and soaked for 1 hour. The disks were removed from solution, placed on Teflon coated aluminum foil, and placed in the oven at 60° C. for 1 hour to dry.

Use as High Capacity Electrode

The following experiments demonstrate the use of PEDOT:PSS/cellulose electrodes (formed using the present techniques) at high voltages. All experiments use the PEDOT:PSS/cellulose electrodes as 4 mm disks in either an e-cube device or e-lysis device.

(1) E-lysis experiment: The purpose of this experimental work was to develop a continuous-flow electrified microfluidic structure that would allow for the release of DNA from, in particular, eukaryotic cells. The mechanism for this release was the application of an electric field, sufficiently strong enough to not only create cell wall permeability, but to also allow release of DNA from within the cell nucleus. While electroporation is commonly used to reversibly increase permeability of the cell plasma membrane, electric field strengths (on the order of 2 kV/cm) above the threshold for electroporation results in irreversible electroporation, and rupture of the nuclear envelope.

Figure 9:
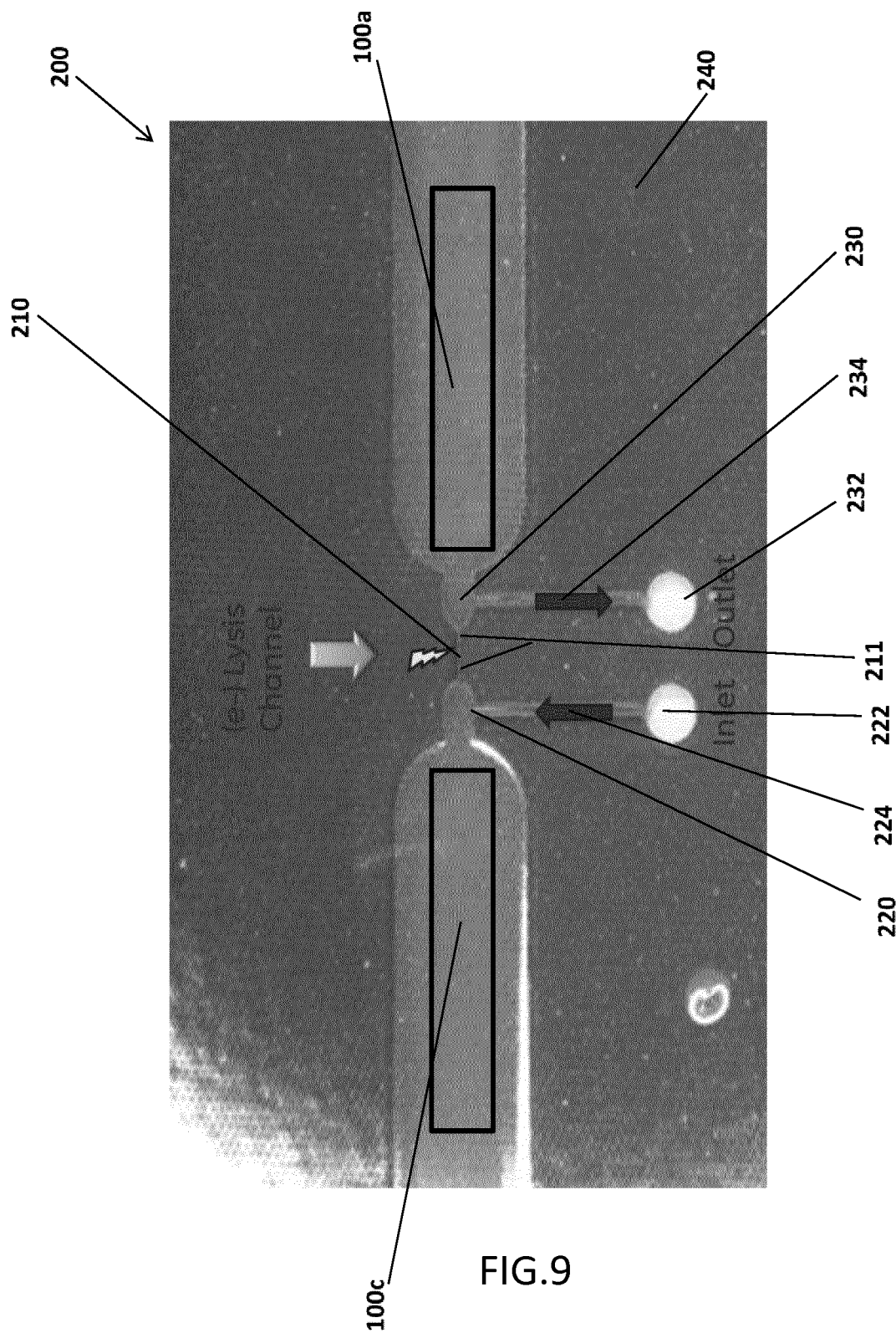
FIG. 9 shows apparatus for cell lysis constructed in accordance with one embodiment and described in more detail below.

The device 200 used to conduct e-lysis testing is illustrated in FIG. 9 and consists of a channel 210 constructed by a thin film lamination process. The channel 210 has a volume bounded by a floor, sides, and ceiling of the channel 210, and was constructed from YAG laser-profiled, 2 mil thick Kapton polyimide. They were bonded through the use of 0.5 mil Pyralux LF, a B-staged acrylic sheet adhesive and further sandwiched between two blocks of ABS plastics 240. An inlet 220 and an outlet port 230 at opposing ends of the channel 210 lead to an inlet 222 and an outlet 232 via fluidic pathways 224 and 234 respectively in the plastics blocks 240. The block allows the introduction of a live cell fluid solution at the inlet 222, and for the removal and collection of lysed solution by applying a pressure differential across the inlet and outlet, either providing a continuous flow from inlet to outlet, or providing an alternating the flow such that multiple passes of the same fluid are made in order to subject the fluid to an electrical potential difference at least more than once for example up to 10 times. Electrodes 100c (cathode) and 100a (anode) are located adjacent the opposing ends of channel 210 in the plastics blocks 240 and are manufactured as described above. The channel 210 was structured so as to include restrictive width sections 211. The restrictive sections 211 serve to locally increase the magnitude of the electric field due to the resistance of electrolyte flow. Through the use of these microfluidic structural aspects, high electrical field intensities are achieved, without the need to position the two electrodes 100c and 100a in extremely close proximity or increase the source voltage to excessive levels. Voltages of between 25 volts and 1000 volts were successful in lysing live cells where up to 90% of cells were lysed. Cells in whole blood samples were also successfully lysed, with around 50% of cells being lysed.

In previous E-lysis work, platinum or gold electrodes had been incorporated into the respective devices. A limitation exists with these electrodes, however, in that substantial gas generation (from water electrolysis) at each electrode surface will occur at high voltages when immersed in an aqueous solution. To avoid this complication, the tested device employed PEDOT:PSS/cellulose electrodes instead of a directly immersed metallic electrodes. A regenerated cellulose membrane was inserted as a barrier between the fluidic channel and the PEDOT electrodes. This served several purposes, including: preventing any loose PEDOT:PSS material from entering the channel, and discouraging cell or DNA binding at the electrodes, while still allowing electrolyte transfer across the membrane between the bulk solution and the electrode surface. During testing, no evidence of hydrolysis/bubble generation was visible.

Figure 6:
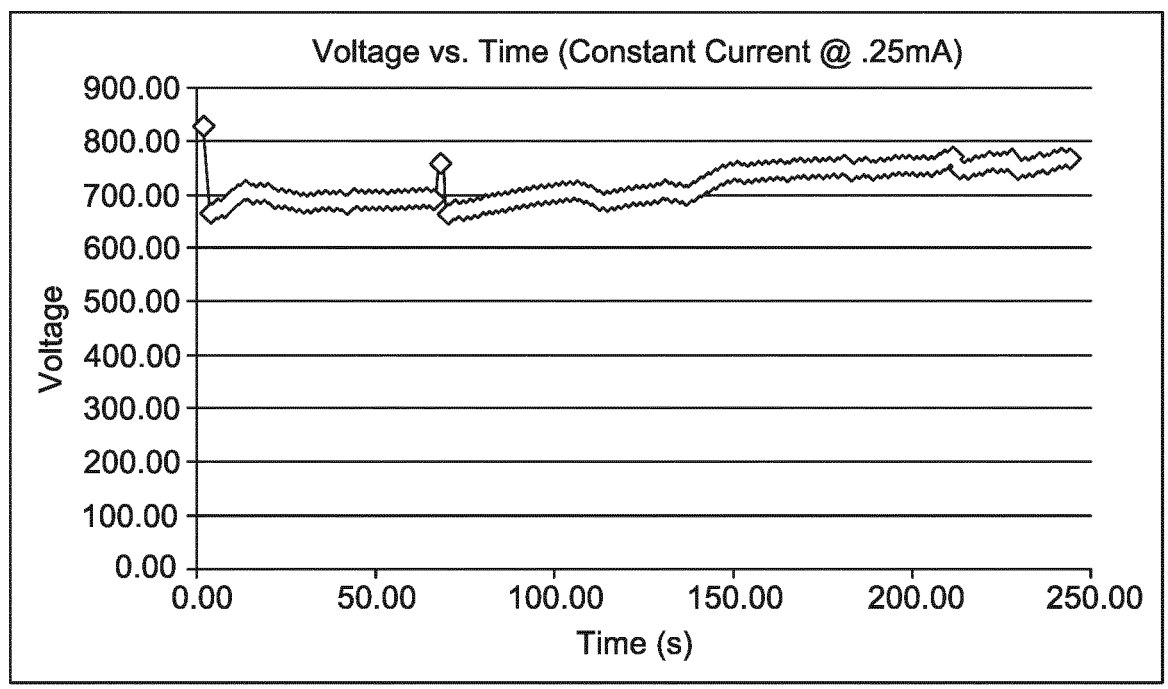
FIG. 6 depicts voltage of time as measured for an electrode generated in accordance with the present approaches.

Since resistance across the PEDOT electrode can vary throughout the test, a constant current was applied to the device. This ensured that the electric field in the lysis channel would remain constant, even if moderate resistance increases occurred in the PEDOT electrodes. Upon applying 0.25 mA of current through the device, the PEDOT:PSS electrodes maintained a voltage between 700-800 V over 4 minutes, as shown in FIG. 6.

(2) High Voltage Testing of PEDOT:PSS in E-Cube: General electrochemical experiments were done in e-cube device. Electrochemical measurements were performed using a Keithley 2410 high-voltage source meter. Data was recorded using either LabView or LabTracer. TE (i.e., Tris+EDTA buffer) was used as the solvent/electrolyte in all electrochemical measurements. TE buffer was prepared to contain 10 mM Tris and 0.1 nM EDTA in distilled water. Electrochemical measurements were performed in an e-cube device where two PEDOT:PSS/cellulose electrodes (4 mm diameter) were placed inside the device, separated by a defined distance, with a regenerated cellulose membrane (Ultracell 3 KDa; Millipore) in between the electrode and the sample/elution chamber. A flow rate of 100 μL/min of TE buffer through the sample chamber was used in all electrochemical experiments performed in the e-cube. Either upchurch connectors or stainless steel screw connectors were used to contact the PEDOT:PSS/cellulose 4 disks in the device. The upchurch connectors were assembled with a copper wire in contact with a plug of PEDOT:PSS/cellulose at the tip of the connector. The lead from the power source was connected to the copper wire and the exposed tip of the copper connector was in contact with the PEDOT:PSS/cellulose electrode disk in the device.

Figure 7:
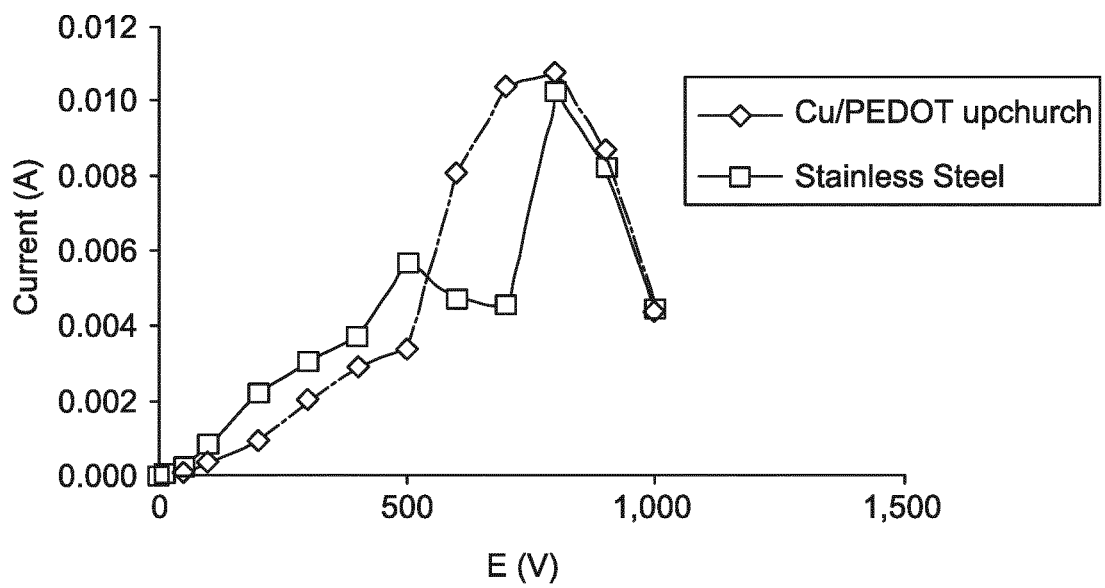
FIG. 7 depicts a current voltage distribution as measured for an electrode generated in accordance with the present approaches.

(a) I/V Curves of PEDOT:PSS electrodes in e-cube device: The current response of increasing voltages applied to PEDOT:PSS/cellulose electrodes in the e-cube device were recorded to determine the voltage at which the electrodes behaved in a linear manner, as shown in FIG. 7. The voltage range examined was between 0 V and 1,000 V. A positive voltage was applied for 3 seconds and the data plotted was at t=1 s. After the positive voltage was applied, a negative voltage of the same magnitude was applied for 3 seconds to recharge the PEDOT:PSS electrodes. The electrodes displayed generally linear behavior up to approximately 500 V, at which time the current recordings became variable. It is assumed that in the e-cube configuration that the PEDOT:PSS had been consumed at this point.

Figure 8:
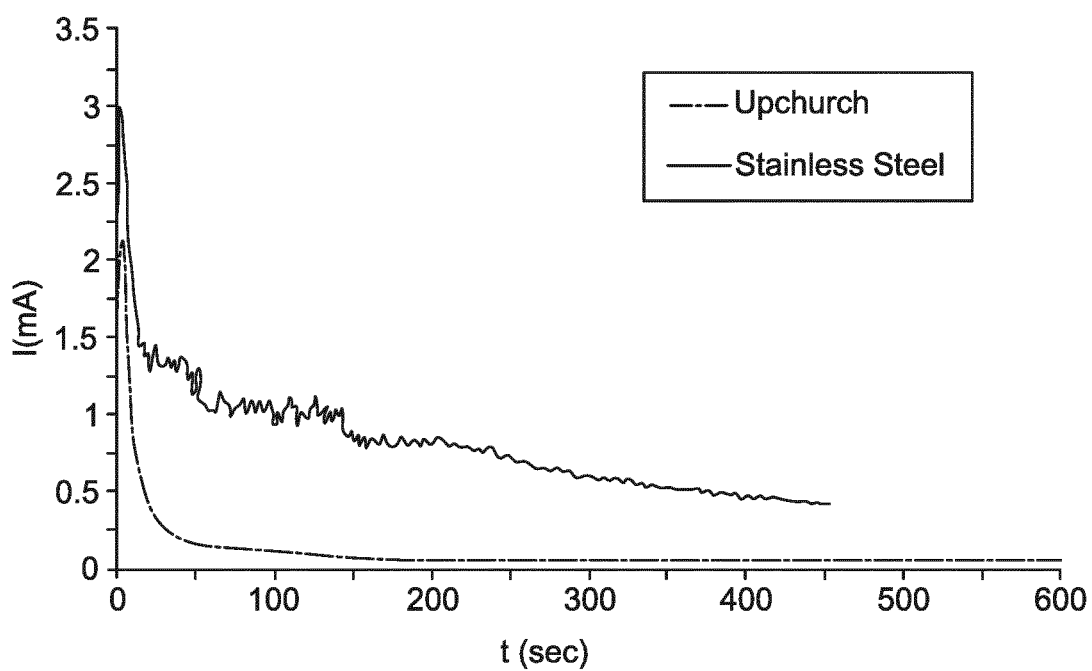
FIG. 8 depicts current over time as measured for an electrode generated in accordance with the present approaches.

(b) Constant Voltage experiment: Measurement of current (I) over time across PEDOT:PSS/cellulose electrodes was performed in an e-cube device at constant voltage to determine the lifetime of the PEDOT:PSS electrodes. Turning to FIG. 8, a graph is shown of the measured current as a function of time as a potential of 200 V is applied and TE buffer is flowed through the device at a rate of 100 μL/min.

Samples containing cells which had been electrically lysed in accordance with the methods described above were further processed by known techniques, including purification and DNA amplification, for example via a chain polymerase reaction and were found to provide acceptable results, indicating that the electrical lysis techniques described herein are a suitable substitute for known chemical lysis techniques. In particular, the electrical lysis techniques described herein have been found to provide high efficiency lysing of cells, i.e. effective and efficient lysing of high volumes and high cell numbers of cells. For example with 100 uL/min flow rate through channel 210 (FIG. 9), with $1.5 \times 10^6$ cells/mL, using 1000V/cm potential difference, cell lysis of about 80-90% was observed.

Technical effects of the invention include, but are not limited to, a redox electrode capable of being used at voltages greater than 25 V, such as between about 25 V to about 1,000 V. Technical effects also include an electrode formed using hybrid materials, such as a conducting polymer coated onto or combined with textile fibers, plastics, or polymers. Technical effects also include electrodes manufactured using redox polymers on a cellulose support.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An oxidation-reduction (redox) electrode, comprising:
   a support substrate comprising cellulose fibers; and
   a redox polymer comprising poly(3,4-ethylenedioxythiophene): polystyrene sulfonate (PEDOT:PSS) blended in a slurry with the support substrate fibers and dried in a mold to produce the redox electrode, wherein the redox polymer has a thickness greater than 1 micron with respect to a surface of the support substrate,
   wherein the slurry is 5-25 wt % PEDOT:PSS.

2. The redox electrode of claim 1, wherein the support substrate comprises textile fibers, a plastic substrate, or a polymer substrate.

3. The redox electrode of claim 1, further comprising an ionic cross-linking agent.

4. The redox electrode of claim 3, wherein the ionic cross-linking agent comprises $MgSO_4$.

5. The redox electrode of claim 1, further comprising an ionomer coating.

6. The redox electrode of claim 1, further comprising:
   a metallic wire, foil, or mesh about which the support substrate and redox polymer are disposed.

7. The redox electrode of claim 1, wherein the slurry is 14-18 wt % PEDOT:PSS.

* * * * *